and Townsend

United States Patent [19]
Hramchenko et al.

[11] 3,944,506
[45] Mar. 16, 1976

[54] ABRADANT SKIN CLEANSER CONTAINING A BORATE SALT

[75] Inventors: Jack Hramchenko, Menlo Park; Murray J. Sibley, Berkeley, both of Calif.

[73] Assignee: Barnes-Hind Pharmaceuticals, Inc., Sunnyvale, Calif.

[22] Filed: Aug. 17, 1973

[21] Appl. No.: 389,297

[52] U.S. Cl. .............. 252/526; 252/135; 252/532; 252/538; 252/DIG. 5; 424/148
[51] Int. Cl.² .. A61K 7/50; C11D 1/83; C11D 3/04; C11D 3/14
[58] Field of Search ...... 252/DIG. 5, 106, 107, 135, 252/526, 532, 538; 424/148

[56] References Cited
UNITED STATES PATENTS

| | | | |
|---|---|---|---|
| 1,362,393 | 12/1920 | Chaplin | 252/DIG. 5 |
| 1,703,602 | 2/1929 | Sokoloff | 252/DIG. 5 |
| 2,374,187 | 4/1945 | Flett | 252/DIG. 5 |
| 3,192,166 | 6/1965 | Smith | 252/532 X |
| 3,477,951 | 11/1969 | Malmer | 252/106 |
| 3,671,545 | 6/1972 | Halpern | 252/106 X |

*Primary Examiner*—Dennis L. Albrecht
*Attorney, Agent, or Firm*—Townsend and Townsend

[57] ABSTRACT

Improved water soluble abradant skin cleanser is provided comprising in a non-oleaginous hydrous cream base a sparingly soluble relatively soft non-toxic non-irritating particulate salt, a non-irritating, non-toxic surfactant as a stable cream base, employing at least one derivative of sulfuric acid, e.g. sulfate ester salt or sulfonate and water. In a preferred embodiment, borax is combined with a substantial amount of an alkyleneoxy sulfate ester salt or tauride salt and a small amount of water. The cleanser aids in the treatment of oily skin, acne and scalp conditions.

12 Claims, No Drawings

3,944,506

ABRADANT SKIN CLEANSER CONTAINING A BORATE SALT

BACKGROUND OF THE INVENTION

1. Field of the Invention

Acne is the sum total of the consequences of over activity and disorder activity of the oil producing or sebaceous glands of the skin. Adolescence is the time of life when sebaceous glands tend to be at peak activity. Aberrative conditions can also enhance sebaceous activity. As a result of a series of phases, beginning with the formation of a comedo, the comedo develops into a papule, which may then become a pustule, followed by a cyst, and finally the formation of scar tissue. Each of the phases is unsightly and can be embarrassing to a youth concerned with his or her appearance.

While the etiology of the various phases of the acne condition which was described above is not definitely known, it is known that the comedo is a plug which is the initial phase of the acne condition. The formation of the comedo is related to the oiliness of the skin. Therefore, varying efforts have been made to enhance the removal of the oil from the skin, so as to minimize the formation of the comedo.

Synthetic detergents have been employed, with or without added keratoplastic and keratolytic agents. While these have been helpful in some cases, they have often been extremely drying and have failed to accomplish the desired desquamation. Topically applied abrasives and keratolytic materials have been used also for the treatment of acne. Frequently, while these agents have been found to be therapeutic, they have also been extremely irritating to the skin. Furthermore, the abrasives have tended to give a reddish meat like coloration to the skin which is undesirable. Also, the small abrasive particles can become embedded in the follicles and skin, be difficult to remove, and act as plugs in the pores aiding in the pathogenesis of acne.

2. Description of the Prior Art

U.S. Pat. No. 3,092,111 describes an abrasive paste composition employing a hard abrasive. U.S. Pat. No. 2,494,827 discloses detergent composition employing water-insoluble crystalline metaphosphates which are made soluble by using combinations of cations. Other patents describing skin care lotions include U.S. Pat. Nos. 1,073,787, 1,452,093, 1,703,602, 2,581,278 and 3,062,721.

SUMMARY OF THE INVENTION

Novel hydrous abradant cream cleanser compositions are provided for treatment of oily skin and acne comprising relatively soft, fine mesh inorganic particles, which are sparingly soluble in water, substantially uniformly dispersed in a stable cream base. In particular, borates or other inorganic salts of comparable properties are dispersed as a particulate in a sulfate or sulfonate surfactant cream base containing a small amount of water. The subject creams have long shelf life, provide a mild abrasive cleansing effect and rapidly dissolve upon rinsing of the skin.

DESCRIPTION OF THE SPECIFIC EMBODIMENTS

Novel abradant cleansing creams are provided having substantial amounts of a relatively soft abradant particulate sparingly soluble inorganic salt in a surfactant cream base containing water. Small amounts of other materials may also be included to enhance the properties of the cream base. The significant ingredients in the composition are, therefore, the inorganic abradant salt, the surfactant composition and water.

The compositions are found to be stable for long periods of time, as evidenced by accelerated tests.

The subject compositions do not liquefy on storage nor does the inorganic particulate material settle out. The composition retains its desirably creamy texture for long periods of time. In addition, the inorganic particulate matter retains its abradant activity, but responds to water flooding by dissolving at a reasonable rate. The composition has desirable foaming characteristics, despite the foam inhibiting effect of the inorganic particulate matter.

By reason of the excellent properties of the subject composition, when taken from the container and used, an abradant effect is obtained from the inorganic particles, while the surfactant aids in the removal of oil and dry skin released as a result of the action of the inorganic abradant. After the skin has been sufficiently abraded, by rinsing with increasing amounts of water, the inorganic particles rapidly dissolve leaving the skin fresh and clean, free of oil and dead skin. The salt must be sparingly soluble in water, normally being soluble in water in an amount of less than about 30 weight percent at 40°C and less than about 10 weight percent at 20°C. The salt should be soluble in water at 20°C in at least 0.5, usually at least 1 weight percent and, preferably, at least about 3 weight percent. The salts must be nontoxic and nonirritating to the skin.

The particles will normally be of about 20–200 mesh and usually at least 100μ. Mixtures of particles may be employed including particles of a size up to about 3,500μ, more usually of up to about 3,000μ. Preferably, the average particle size will be in the range of about 125 to 750μ.

The inorganic salts will generally have a hardness less than 6 Mohs and greater than 1 Moh, usually from about 1.5 to 4 Mohs. The hardness and size of the particles are both significant in the ability of the particles to remove or abrade dead skin from the skin surface. The size of the particles will also affect the rapidity at which the particles dissolve upon rinsing of the skin. Therefore, the more soluble the inorganic salt, generally, the more preferable the larger size particles.

The salt must be able to retain its character in the presence of water and surfactant, so that upon standing, the salt still retains its particulate character. Fluctuations in temperature on standing should not significantly modify the original size and nature of the particles so as to substantially change the physical character of the salts. Upon contact with gross amounts of water, the particles should dissolve at a moderate rate rather than substantially instantaneously. In this manner, a controlled abradant effect is achieved as one partially removes the cleanser and skin debris, while still retaining a substantial proportion of abradant particles.

The salts which are employed will be primarily alkali metal salts, particularly sodium and potassium, and more particularly sodium. The anion will normally be a complex anion, such as borate. Particular salts are sodium tetraborate, decahydrate (borax) and potassium pentaborate octahydrate. The borax is particularly preferred, because of its excellent shelf life and retention of its original physical properties in combination with the other materials employed.

The next material employed is the surfactant, which may be a single surfactant or a mixture of surfactants.

As the major component of the surfactant, a sodium salt of a derivative of sulfuric acid is preferred, particularly sulfonates and sulfates, more particularly alkyl sulfonates.

The preferred sulfates and sulfonates come under the classification, "Foaming Agents." Chester, International Review of the Cosmetic, Perfumery, Detergent and Allied Industries, 46, 205 (1973); the article is entitled, The Function of Cosmetic Components. The sulfates and sulfonates are anionic foaming agents.

In combination with the anionic foaming agents may be employed nonionic surfactants, e.g. polyalkyleneoxy compounds, either etherified or esterified, where the alkylene group is of from 2 to 3 carbon atoms.

The sulfate and sulfonate foaming agents which are employed are for the most part conventional sulfates and sulfonates which are used to prepare creams. The foaming agents have the desired viscosity and feel properties associated with creams and are normally recommended by their suppliers for this purpose. They are frequently supplied as aqueous concentrates and upon the addition of the particulate inorganic salt to form the compositions of this invention, there is a significant enhancement of the viscosity of the medium. Therefore, the surfactant employed should have an initial viscosity which is sufficiently low, so that upon the addition of the inorganic salt, the desired texture is achieved or, alternatively, other additives may be included which serve to modify the viscosity or flow properties of the cream.

The sulfate ester salts will normally be sodium salts of the monoesters of sulfuric acid having one or more alkyleneoxy groups, usually not more than about 4, more usually not more than about 3, having the other hydroxy group etherified or esterified with a fatty acid or alkyl of at least about 10 carbon atoms, usually at least 12 carbon atoms and normally not more than 18 carbon atoms. The preferred sulfate esters are those having polyethyleneoxy groups having from 2 to 3 units, with the hydroxyl group etherified with a fatty alkyl of from 12 to 18 carbon atoms, more usually of from 12 to 16 carbon atoms.

The sulfonates are usually alkyl sulfonates, particularly taurides, where the amino group is disubstituted, one of the substituents being a fatty acid group of from 12 to 18 carbon atoms, more usually of from 14 to 18 carbon atoms and the other substituent being a lower alkyl group of from 1 to 3 carbon atoms, and usually methyl. The taurine derivatives are particularly preferred because of their creamy texture and the excellent properties of the combination of borax and the taurine derivative.

In addition to the sulfuric acid derivative detergent or surfactant, numerous other surfactants or emulsifiers may also be included in minor amounts. Of the nonionic surfactants or emulsifiers, these will normally be polyols, such as polyethyleneoxy, polypropyleneoxy, or combinations thereof, which may be further etherified or esterified and serve to affect the viscosity, feel, stability, etc. of the cream. Particularly, fatty acid esters of polyols, e.g. glycerol monopalmitate and polyethyleneoxy oleate, find use. The polyols will usually have 2 to 3 alcoholic groups. The nonionic surfactants will usually have HLB values in excess of 7 and generally less than 18. The nonionic surfactants not only aid surfactantcy, but enhance both physical and subjective characteristics of the cream to enhance its popular acceptability. The high molecular weight polyalkyleneoxy compounds also provide thickening. These compounds will normally have molecular weights in the range of 600 to 12,000.

In addition to nonionics, anionic surfactants may also be employed for modifying the viscosity, enhancing surfactantcy, or enhancing foaming. Illustrative of this type of compound is the sodium salt of laurylsulfoacetate.

Finally, neutral amides may also be used such as hydroxyalkylated fatty acid amides, e.g. n-hydroxypropyl or di(hydroxyethyl) lauramide or myristamide. These compounds serve as foam stabilizers (nonionic). Chester, supra.

In addition to the above components, there will normally be a number of additional additives to fulfill specific purposes. These additives include bacteriostats or bacteriocides, therapeutic agents, e.g. anti-dandruff, colorants, perfumes, fatty materials, particularly fatty acids and fatty alcohols of from 8 to 18 carbon atoms to enhance feel, and the like, e.g. cetyl alcohol.

Of the total composition, the inorganic particulate matter will vary from about 20 to 80 weight percent, preferably from about 25 to 60 weight percent and more preferred from about 35 to 60 weight percent.

The sulfuric acid derived surfactants or foaming agents will generally comprise at least 10, usually at least 15, generally not more than 60 and usually not more than about 50 weight percent of the total composition. Of the cream composition (excluding the inorganic salt) the surfactant will generally be in the range of about 15 to 70 weight percent, more usually in the range of about 20 to 60 weight percent.

When the sulfonate e.g. tauride, is the major component of the surfactant, the sulfonate will normally be present in from 10 to 50, usually 10 to 30, weight percent of the cream composition. When the sulfate e.g. fatty alkyl polyoxyalkylene sulfate ester salts, is the major component, the sulfate will normally be present in from about 20 to 70, usually 30 to 60, weight percent of the cream composition.

The water will be as initially added at least 3 weight percent of the total composition, more usually at least 5 weight percent of the total composition and generally not exceed 50 weight percent of the total composition, more usually not exceeding about 40 weight percent of the total composition. Preferably, the amount of water will be in the range of about 10 to 30 weight percent. By initially added is intended that any dehydrating effect of the salt or other materials is ignored and the amounts refer to that amount of water initially incorporated into the composition which is added as other than waters of hydration. Of the cream composition, the water will generally range from about 5 to about 65 weight percent, more usually from about 30 to 60 weight percent. While greater amounts of water may be added, particularly with materials at the lower range of water solubility, the higher amounts of water will usually reduce shelf life.

The nonionic materials will be added as required to achieve the desired viscosity, feel or other improved properties. The nonionic materials will normally be employed in relatively small amounts usually not exceeding 12 weight percent of the total composition, more usually not exceeding 10 weight percent of the total composition and generally being employed in at least about 2 weight percent of the total composition, when employed. In the cream, the nonionic materials will generally be present in from about 2 to 20 weight percent, more usually from about 3 to 12 weight percent.

The minor additives will be added in small but effective amounts, generally not totaling greater than 15 weight percent, more usually totaling not greater than about 12 percent of the cream composition. Individual additives will generally range from about 0.01 weight percent to 8 weight percent, more usually from about 0.05 weight percent to about 6 weight percent of the cream composition. Foam boosters and hair conditioners may range from 1 to 8 weight percent of the cream compositions.

The cream compositions can be readily prepared by mixing the various ingredients at an elevated temperature with agitation, followed by emulsification by mixing with a high speed shearing mixer. Normally, the ingredients are added incrementally in accordance with their solubility properties so that at each stage the materials are completely dissolved or homogeneously dispersed. When formation of the cream is completed, and temperature reduced to below 40°C, the inorganic salt may be added with agitation so as to homogeneously disperse the inorganic salt.

In order to demonstrate the subject invention, the following compositions were prepared and their properties tested under a variety of conditions.

Example 1 was prepared as follows: Arlacel-165, Standamul 0-20 and Irgasan DP-300 were heated to about 65°C with agitation. Steol 4N, potassium sorbate, and Maypon UD were combined at 65°C with agitation, followed by the addition of the color solution, when the potassium sorbate had dissolved. The two mixtures were then combined and agitated for three minutes, whereupon 10 percent of the Igepon TC42 was added with increasing agitator speed to provide emulsification. After allowing the mixture to cool to about 35°–40°C, the remainder of the Igepon TC42 was added gradually, followed by the addition of Lathanol LAL at a relatively low speed. The perfume was then added with low agitation followed by the addition of the borax with low agitation.

Examples 2 to 5 were prepared as follows. The Arlacel-165 and cetyl alcohol were combined and heated at about 60°C, followed by the addition of Standapol ES 40 concentrate while maintaining the temperature with agitation. The heat was removed and the Standapol CS shampoo base added while agitating at a moderate speed until the mixture cooled to room temperature. The pH was then adjusted to 5.2 with 0.1 percent citric acid. Borax was added with mild agitation.

The remaining examples were prepared in accordance with the procedures previously described, except that Example 8 was adjusted to pH 6.4 with citric acid.

The compositions prepared were all found to be stable at room temperature for long periods of time, showed excellent abradant or scrubbing characteristics

| Ingredients[1] | parts by weight | | | | | | | | | |
|---|---|---|---|---|---|---|---|---|---|---|
| Sulfates | 1 | 2 | 3 | 4 | 5 | 6 | 7 | 8 | 9 | 10 |
| Igepon TC42 (active) | 10.5 | | | | | 21 | 21.4 | 24.2 | 19.6 | 20.6 |
| Steol 4N (active) | 3 | | | | | | | 6.4 | | |
| Standapol CS (active) | | 25.5 | 25.5 | 25.5 | 25.5 | | | | | |
| Standapol ES-40 (active) | | 31.2 | 31.2 | 31.2 | 31.2 | | | | | |
| Standapol ES-2 (active) | | | | | | 6.25 | 7.5 | | | |
| Lathanol LAL | 5 | | | | | | | | | |
| non-ionics | | | | | | | | | | |
| Arlacel 165 | 3.5 | 4 | 4 | 4 | 4 | 9.8 | 4.9 | 7.8 | 9.8 | 9.8 |
| Standamul O-20 | 0.225 | | | | | 2 | 1 | | 4.9 | 3.9 |
| Pluronic F-68 | | | | | | | | | 3 | 3 |
| Standamid LD | | | | | | | | | 2 | |
| Pluronic L-61 | | | | | | | | | | 3 |
| Standamid SD | | | | | | | | | | |
| Abradant | | | | | | | | | | |
| Borax (40–100 mesh) | 50 | 11 | 25 | 150 | 400 | 66.7 | 66.7 | 66.7 | 66.7 | |
| K pentaborate octahydrate | | | | | | | | | | 66.7 |
| Water | 27.3 | 37.8 | 37.8 | 37.8 | 37.8 | 58 | 62.3 | 61.6 | 53.9 | 54.6 |
| Miscellaneous | | | | | | | | | | |
| Cetyl alcohol | | 1.5 | 1.5 | 1.5 | 1.5 | 3 | 3 | | 4 | 4 |
| Irgasan DP300 | 0.09 | | | | | | | | | 0.2 |
| K sorbate | 0.09 | | | | | | | | | 0.2 |
| Maypon UD | 0.15 | | | | | | | | 1.7 | 0.7 |
| Color and Perfumes | 0.35 | | | | | | | | 1.0 | |
| Triethanolamine | | | | | | | | | | |

[1]Sulfonates

| | |
|---|---|
| Igepon TC42 (35% active) | sodium N-coconut N-methyl tauride |
| Steol 4N (27–29% active) | sodium lauryl polyoxyethylene sulfate (vis-31 cps, 25°C) |
| Standapol CS (60% active) | partially sulfated fatty acid polyethyleneoxy ether neutralized |
| Standapol ES-40 (>58% active) | sodium myristyl triether sulfate |
| Standapol ES-2 (>25% active) | sodium lauryl diethyleneoxy sulfate |
| Lathanol LAL | sodium lauryl sulfoacetate |
| Non-ionics | |
| Arlacel 165 | glycerol monostearate + polyethyleneoxy stearate |
| Standamul O-20 | polyoxyethylene (20) oleyl ether |
| Pluronic F-68 | polyethyleneoxy polypropyleneoxy condensate (8,350 avg. m.w.) |
| Standamid LD | lauric (70) myristic (30) diethanolamide |
| Pluronic L-61 | polyethyleneoxy polypropyleneoxy condensate (2,000 avg. m.w.) |
| Standamid SD | modified coconut fatty acid diethanolamide |
| Miscellaneous | |
| Irgasan DP300 | antibacterial phenolic ether |
| Maypon UD (35% active) | hair treatment — anti-dandruff |

—dissolved at a reasonable rate when flooded with water—had good to excellent foaming characteristics and retained their creamy texture and desirable feel. Besides the long term shelf life at ambient conditions, some of the compositions showed excellent stability under elevated temperature accelerated aging conditions. Those compositions which had relatively short lives under the severe elevated temperature test could be improved by the addition of small amounts of viscosity index improvers.

Physical stability tests were carried out as follows on Examples 6 to 9. The mixtures were heated for a period of time at 40°C and any changes in the composition noted at the end of the time. The following indicates the results obtained.

Example 6 after 7 weeks, the texture had softened and the particles were unchanged;

Example 7, after three weeks, the base had liquefied indicating the desirability of a greater amount of thickener.

Example 8, after three weeks, the texture and particles wereuunchanged;

Example 9, after one month, the texture had softened on the surface and the particles were unchanged.

A study was carried out employing the formulation of Example 1. Borax particles by themselves of the same mesh (40–100) as the borax particles employed in the formulation were stirred for 90 secs. with varying amounts of water at 45°C and the percent by weight of the particles remaining after being stirred with water was determined. The formulation was stirred with water for only 60 secs. The amount of water varied from 2.5 to 12.5ml of water, and the weight of borax was 1.3g, while the weight of the formulation was 2gm. While a somewhat greater weight percent of the particles in the formulation did not dissolve at the lower levels of water, above 5ml of water, the percent dissolved was substantially the same. Therefore, the borax present in the formulation would dissolve as the face is rinsed, since the solubility properties of the borax were not significantly modified by the presence of the various ingredients in the formulation.

In a second study, the borax and the formulation employed above were mixed with 15ml of water and the percent of the borax remaining at various times determined. It was found that the borax in the formula dissolved somewhat more rapidly then borax by itself, being gone in about 60 seconds, while the borax by itself was substantially gone in 75 seconds. Significantly, there was still a substantial amount of borax after 20 seconds, in excess of ten percent of the original amount, so that as a person rinsed his face, the borax would not disappear instantaneously, but would continue to provide abradant action. Thus, one would obtain the surfactantcy and abradant action for a reasonable period of time to insure a thorough scrubbing of the face, without irritation or meaty appearance.

The subject compositions provide a therapeutic means for treating oily skin and acne. The compositions are stable for long periods of time, with the abradant material maintaining its abradant character. Good foaming characteristics are retained. The compositions can be smoothly and uniformly applied to the skin providing for mild abrasion of the skin, without irritation or significant reddening of the skin. In this manner, dead skin can be removed, as well as other debris, oil removed, and the pores cleansed of minor residues which may have become deposited in the skin.

Because of the solubility of the abradant cleanser, none of the particles will be captured and retained in any of the pores, nor need there be any concern in removing the abradant particles, which has proved annoying with non-soluble abradant particles. Also, because the particles are sparingly soluble, the amount of abrasive action can be varied in accordance with the user. Thus, by controlling the amount of rinsing water, prolonged or short term abradant treatment can be applied.

Although the foregoing invention has been described in some detail by way of illustration and example for purposes of clarity of understanding, it will be obvious that certain changes and modifications may be practiced within the scope of the appended claims.

What is claimed is:

1. An abradant skin cleansing cream consisting essentially of: from 20 to 80 weight percent of a slightly water soluble, non-toxic physiologically acceptable inorganic salt of a size in the range of about 20 to 200 mesh having a hardness greater than 1 Moh, said inorganic salt being a sodium or potassium tetraborate or a sodium or potassium pentaborate;

and from 80 to 20 weight percent respectively of a cream composition comprising from about 15 to 70 weight percent of a sodium salt of an anionic foaming agent based on a sulfuric acid anion; and an amount of water from 5 to 65 weight percent of said cream composition and substantially less than the amount required to dissolve said inorganic salt at ambient temperature.

2. A composition according to Claim 1, wherein said inorganic salt is borax.

3. A composition according to claim 2, wherein said anionic foaming agent is a tauride.

4. A composition according to claim 2, wherein said anionic foaming agent is an alkylether of an alkyleneoxy sulfate ester.

5. An abradant skin cleansing cream composition comprising:

from 20 to 80 weight percent of borax of a particulate size in the range of about 20 to 200 mesh and from 80 to 20 weight percent respectively of a cream base composition comprising:

from 15 to 70 weight percent of a sodium salt of a foaming anionic surfactant; from 5 to 65 weight percent of water as initially added; up to 12 total weight percent of at least one polyol, polyol ester or polyol ether nonionic surfactant.

6. A composition according to claim 5, wherein said borax is present as particles of a size in the range of $100\mu$ to $3,500\mu$ and in an amount of 25 to 60 weight percent and said cream composition is present in an amount of from 40 to 75 weight percent respectively, said anionic foaming agent includes a tauride which is present in from about 10 to 50 weight percent of said cream composition, said water is present in from about 20 to 60 weight percent of said cream composition, and said nonionic surfactant is present in from about 3 to 12 weight percent of said cream composition and is a polyol fatty acid ester.

7. A composition according to claim 5, wherein said borax is present in from about 25 to 60 weight percent of the total composition and said cream composition is present in from about 40 to 75 weight percent of the total composition, said anionic foaming agent includes fatty alkyl polyoxyalkylene sulfate ester sodium salts which are present in from about 20 to 70 weight percent of said cream composition; said water is present in from about 5 to 65 weight percent of said cream composition and said nonionic surfactant is present in from about 3 to 12 weight percent of said cream composition and is a polyol fatty acid ester.

8. A composition according to claim 5, having a small but sufficient amount of sodium lauryl sulfoacetate.

9. An abradant skin cleansing cream composition having from 35 to 60 weight percent of borax of an average particle size in the range of about 125 to 750µ and from 40 to 65 weight percent of a cream base composition comprising from about 10 to 50 weight percent of a sodium tauride anionic foaming agent; from about 3 to 12 weight percent of a polyol fatty acid ester nonionic surfactant; and from about 40 to 60 weight percent water.

10. A composition according to claim 9; wherein said tauride is sodium N-coconut N-methyl tauride; and having as a foam booster from 0.5 to 8 weight percent of said cream composition of sodium lauryl sulfoacetate.

11. An abradant skin cleansing cream composition comprising from about 35 to 60 weight percent of borax having an average particle size in the range of about 125 to 750µ and from 40 to 65 weight percent of a base cream composition comprising from about 30 to 60 weight percent of sodium polyalkyleneoxy sulfate ester anionic foaming agents; from about 3 to 12 weight percent of a polyol fatty acid ester; and from about 30 to 60 weight percent of water.

12. A composition according to claim 11, wherein said sulfate ester is at least one of the group consisting of sodium myristyl triethyleneoxy sulfate and sodium lauryl polyethyleneoxy sulfate.

* * * * *